US009823256B2

(12) United States Patent
Waugh et al.

(10) Patent No.: US 9,823,256 B2
(45) Date of Patent: Nov. 21, 2017

(54) CXCR1 AS A PREDICTOR OF RESPONSE TO TREATMENT WITH EPIDERMAL GROWTH FACTOR RECEPTOR THERAPEUTIC

(75) Inventors: David John James Waugh, Bangor (GB); Richard Wilson, Belfast (GB); Olabode Oladipo, Belfast (GB)

(73) Assignee: The Queen's University of Belfast, Belfast (GB)

( * ) Notice: Subject to any disclaimer, the term of this patent is extended or adjusted under 35 U.S.C. 154(b) by 236 days.

(21) Appl. No.: 14/113,783

(22) PCT Filed: Apr. 25, 2012

(86) PCT No.: PCT/GB2012/050906
§ 371 (c)(1),
(2), (4) Date: Dec. 31, 2013

(87) PCT Pub. No.: WO2012/146919
PCT Pub. Date: Nov. 1, 2012

(65) Prior Publication Data
US 2014/0127689 A1    May 8, 2014

(30) Foreign Application Priority Data
Apr. 26, 2011   (GB) .................................. 1106870.7

(51) Int. Cl.
G01N 33/574    (2006.01)
G01N 33/68     (2006.01)
C12Q 1/68      (2006.01)

(52) U.S. Cl.
CPC ....... G01N 33/6893 (2013.01); C12Q 1/6886 (2013.01); G01N 33/57484 (2013.01); C12Q 2600/106 (2013.01); C12Q 2600/158 (2013.01); G01N 2333/726 (2013.01); G01N 2800/52 (2013.01)

(58) Field of Classification Search
CPC ....... G01N 33/57484; G01N 2333/726; G01N 2800/52; C12Q 1/6886; C12Q 2600/106; C12Q 2600/158
See application file for complete search history.

(56) References Cited

U.S. PATENT DOCUMENTS

| | | |
|---|---|---|
| 5,196,446 A | 3/1993 | Levitzki et al. |
| 5,558,864 A | 9/1996 | Bendig et al. |
| 5,616,582 A | 4/1997 | Barker |
| 5,646,153 A | 7/1997 | Spada et al. |
| 5,656,655 A | 8/1997 | Spada et al. |
| 5,679,683 A | 10/1997 | Bridges et al. |
| 5,891,996 A | 4/1999 | Mateo de Acosta del Rio et al. |
| 6,235,883 B1 | 5/2001 | Jakobovits et al. |
| 2007/0128636 A1 | 6/2007 | Baker et al. |
| 2009/0258364 A1 | 10/2009 | Goel et al. |
| 2011/0053787 A1 | 3/2011 | Brulliard et al. |

FOREIGN PATENT DOCUMENTS

| | | |
|---|---|---|
| WO | WO-91/16051 | 10/1991 |
| WO | WO-9630347 A1 | 10/1996 |
| WO | WO-9633980 A1 | 10/1996 |
| WO | WO-9727199 A1 | 7/1997 |
| WO | WO-9730034 A1 | 8/1997 |
| WO | WO-9742187 A1 | 11/1997 |
| WO | WO-9749688 A1 | 12/1997 |
| WO | WO-9833798 A2 | 8/1998 |
| WO | WO-0018761-AI | 4/2000 |
| WO | WO-0031048 A1 | 6/2000 |
| WO | WO-2005103711 A2 | 11/2005 |
| WO | WO-2010056753 A1 | 5/2010 |
| WO | WO-2010145796 A2 | 12/2010 |

OTHER PUBLICATIONS

FDA fact sheet, "About the Center for Drug Evaluation and Research, Cetuximab and Panitumub", www.fda.gov/AboutFDA/CentersOffices/OfficeofMedicalProductsand Tobacco, downloaded Jul. 16, 2015.*
Oladipo et al., The expression and prognostic impact of CXC-chemokines in stage II and III colorectal cancer epithelial and stromal tissue. Br. J. Cancer 104(3): 480-487, Feb. 1, 2011.*
Hidalgo, S. Malik, et al.; "Inhibition of the Epidermal Growth Factor Receptor (EGFR) by OSI-774, a Specific EGFR Inhibitor in Malignant and Normal Tissues of Cancer Patients"; Clinical Pharmacology, Proceedings of ASCO, vol. 20; 2001; p. 71a.
Liu, Huilong; "Research Progress of EGFR Monoclonal Antibody Treating Colorectal Cancer"; Chinese Clinical Oncology, vol. 13, No. 10; Oct. 2008; pp. 948-953.
Xun, Chen, et al.; "Promising Future Biomarkers for Anti-EGFR Monoclonal Antibody in Colorectal Cancer"; Chinese Clinical Oncology, vol. 15, No. 5; pp. 457-460.
Fry, David W., et al.; "A Specific Inhibitor of the Epidermal Growth Factor Receptor Tyrosine Kinase"; Science, vol. 265; Aug. 19, 1994; pp. 1093-1095.
Varney, Michelle L., et al., "Expression of CXCR1 and CXCR2 receptors iin malignant melanoma with different metastatic potential and their role in interleukin-8 (CXCL-8)-mediated modulation of metastatic phenotype", Clinical & Experimental Metastasis 20, 2003, pp. 723-731.
Gabellini, Chiara, et al., "Functional activity of CXCL8 receptors, CXCR1 and CXCR2, on human malignant melanoma progression", European Journal of Cancer 45, 2009, pp. 2618-2627.
Hussain, Farah, et al., "The expression of IL-8 an IL-8 receptors in pancreatic adenocarcinomas and pancreatic neuroendocrine tumours", Cytokine 49, 2010, pp. 134-140.
Li, Aihua, et al., "Expression of Interleukin 8 and Its Receptors in Human Colon Carcinoma Cells with Different Metastatic Potentials", Clincal Cancer Research, 2001; 7: pp. 3298-3304.
Zhu, YM, et al., "Interleukin-8/CXCL8 is a growth factor for human lung cancer cells", British Journal of Cancer, 2004, vol. 91, pp. 1970-1976.

(Continued)

Primary Examiner — Ruixiang Li
(74) Attorney, Agent, or Firm — Marshall, Gerstein & Borun LLP

(57) ABSTRACT

There is provided a molecular marker CXCR1 for predicting response and survival in subjects afflicted with cancer who would benefit from treatment with and Epidermal Growth Factor Receptor (EGFR) targeted therapeutic.

11 Claims, 13 Drawing Sheets

(56) References Cited

OTHER PUBLICATIONS

Figure 6:
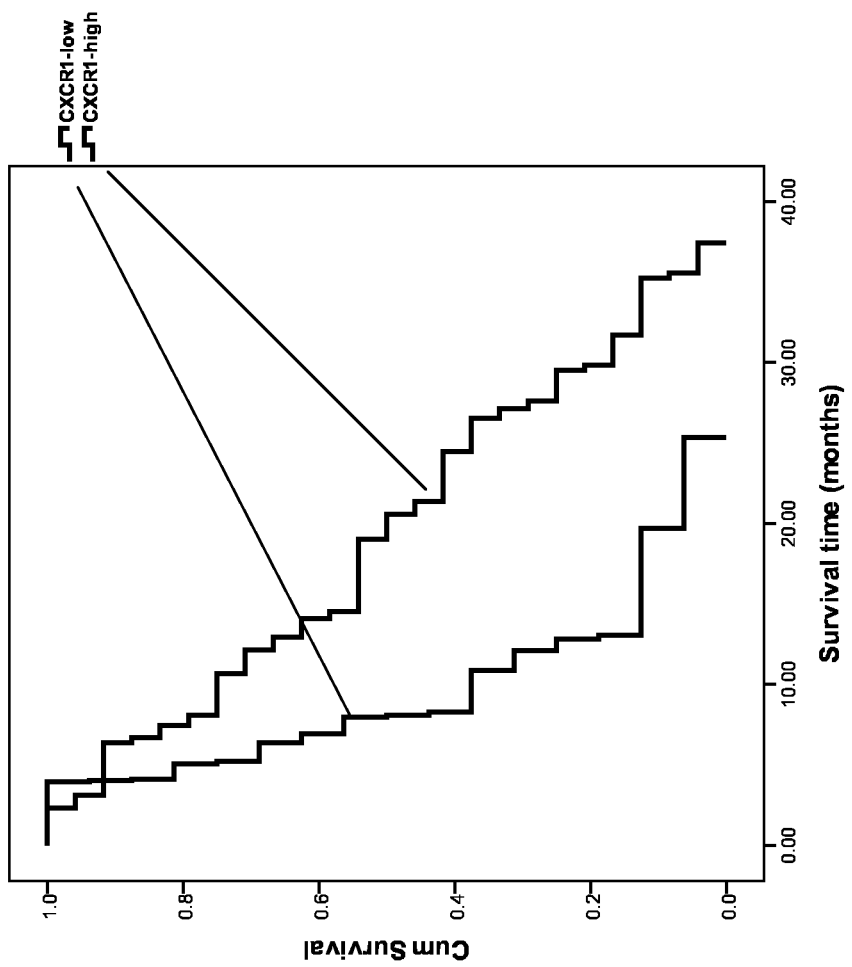

Waugh, David J.J., et al., "The Interleukin-8 Pathway in Cancer", Clinical Cancer Research 14, 2008, pp. 6735-6741.

Chung. Ki Y., et al ., "Cetuximab Shows Activity in Colorectal Cancer Patients With Tumors That Do Not Express the Epidermal Growth Factor Receptor by Immunohistochemistry", Journal of Clinial Oncology, vol. 23, No. 9, Mar. 20, 2005, pp. 1803-1810.

Cunningham, David, et al., "Cetuximab Monotherapy and Cetuximab plus Irinotecan in Irinotecan-Refractory Metastatic Colorectal Cancer", The New England Journal of Medicine 351, Jul. 22, 2004, pp. 337-345.

Itoh, Yusuke, et al., "IL-8 promotes cell proliferation and migration through metalloproteinase-cleavage proHB-EGF in human colon carcinoma cells", Cytokine 29, 2005, pp. 275-282.

Jänne, Pasi A., et al., "Epidermal Growth Factor Receptor Mutations in Non-Small-Cell Lung Cancer: Implication for Treatment and Tumor Biology", Journal of Clinical Oncology, vol. 23, No. 14, May 10, 2005, pp. 3227-3234.

Kyriakakis, Emmanouil, et al., "IL-8-mediated angiogenic responses of endothelial cells to lipid antigen activation of iNKT cells depend on EGFR transactivation", Journal of Leukocyte Biology, vol. 90, Nov. 2011, pp. 929-939.

Maughan, Timothy S., et al., "Addition of cetuximab to oxaliplatin-based first-line combination chemotherapy for treatment of advanced colorectal cancer: results of the randomised phase 3 MRC COIN trial", The Lancet, vol. 377, Jun. 4, 2011, pp. 2103-2114.

Osherov, Nir, et al., "Selective Inhibition of the Epidermal Growth Factor abd HER2/Neu Receptors by Tyrphostins", The Journal of Biological Chemistry vol. 268 No. 15, May 25, 1993, pp. 11134-11142.

Panek, Robert L., et al., "In Vitro Pharmacological Characterization of PD 166285, a New Nanomolar Potent and Broadly Active Protein Tyrosine Kinase Inhibitor", The Journal of Pharmacology and Experimental Therapeutics vol. 283, No. 3, Aug. 4, 1997, pp. 1433-1444.

Saltz, Leonard B., et al., "Phase II Trial of Cetuximab in Patients With Refractory Colorectal Cancer That Expresses the Epidermal Growth Factor Receptor", Journal of Clinical Oncology vol. 22, No. 7, Apr. 1, 2004, pp. 1201-1208.

Venkatakrishnan, Gita, et al., "Chemokine Receptors CXCR-1/2 Activate Mitogen-activated Protein Kinase via the Epidermal Growth Factor Receptor in Ovarian Cancer Cells", The Journal of Biological Chemistry vol. 275, No. 10, Mar. 10, 2000, pp. 6868-6875.

Giry, Murielle, "International Search Report," prepared for PCT/GB2012/050906, dated Aug. 7, 2012, 5 pages.

Zhang, Wu, et al.; "Molecular Predictors of Combination Targeted Therapies (Cetuximab, Bevacizumab) in Irinotecan-Refractory Colorectal Cancer (BONE-2 Study)"; Anticancer Research, vol. 30; Oct. 2010; pp. 4209-4217.

Barrera et al., Cytokine profile determined by data-mining analysis set into clusters of non-small-cell lung cancer patients according to prognosis, *Annals of Oncol.*, 26:428-35 (2015).

Bonneau et al., Predictive markers of chemoresistance in advanced stages epithelial ovarian carcinoma, *Gynecologic Oncol.*, 136:112-20 (2015).

Bustin et al., The MIQE Guidelines: Minimum Information for Publicaton of Quantitive Real-Time PCR Experts, *Clin. Chem.*, 55(4):611-22 (2009).

Chen et al., The IL-8/CXCR1 axis is associated with cancer stem cell-like properties and correlates with clinical prognosis in human pancreatic cancer cases, *Scientific Reports*, 4:5911 (2014).

Kelley et al., Prognostic and Predictive Markers in Stage II Colon Cancer: Is there a role for Gene Expression Profiling, *Clin. Colorectal Can.*, 10(2):73-80 (2011).

Le et al., Prognostic and Predictive Significance of Plasma HGF and IL-8 in a Phase III Trial of Chemoradiation with or without-Tirapazamine in Locoregionally Advanced Head and Neck Cancer, *Clin. Canc. Res.*, 18(6):1798 (2012).

Murphy et al. Nonapical and Cytoplasmic Expression of Interleukin-8, CXCR1 and CXCR2 Correlates with Cell Proliferation and Microvessel Density in Prostate Cancer, *Clin. Can. Res.*, 11(11)::4117 (2005).

Posadas et al., A phase II and Pharmacodynamic study of gefitinib in Patients with refractory or recurrent epithelial ovarian cancer, *Cancer*, 109(7):1324 (2007).

Vergote et al., Randomized phase III study of Erlotinib versus observation in Patients with no evidence of disease progression after first-line platin-based chemotherapy for ovarian carcinoma: A European organization for research and treatment of cancer-gynaecological cancer group, and gynecologic cancer intergroup study, *J. Clin. Oncol.*, 32(4):320 (2014).

\* cited by examiner

FIGURE 1

Table 1.

| | No of Patients (n=116) | % |
|---|---|---|
| Age (years) | | |
| Median | 65 | |
| Range | 35-80 | |
| | | |
| Gender | | |
| Male | 74 | 63.8 |
| Female | 42 | 36.2 |
| | | |
| Study arm | | |
| A | 42 | 36.2 |
| B | 51 | 44.0 |
| C | 23 | 19.8 |
| | | |
| Received Cetuximab? | | |
| Yes | 51 | 44.0 |
| No | 65 | 56.0 |
| | | |
| KRAS status | | |
| Wild-type | 68 | 58.6 |
| Mutant | 38 | 32.8 |
| Not evaluated | 10 | 8.6 |
| | | |
| Response at 12 weeks? | | |
| Yes | 48 | 41.4 |
| No | 53 | 45.7 |
| Not evaluated | 15 | 12.9 |
| | | |
| Response at any time? | | |
| Yes | 50 | 43.1 |
| No | 60 | 51.7 |
| Not evaluated | 6 | 5.2 |
| | | |
| Status | | |
| Dead | 94 | 81.0 |
| Censored | 22 | 19.0 |

FIGURE 2

Table 2. Multivariate logistic regression for response at 12 weeks

| | Odds ratio | P | 95% C.I. for odds ratio | |
|---|---|---|---|---|
| | | | Lower | Upper |
| Tumour epithelial CXCR1 expression | 0.578 | 0.005 | 0.394 | 0.848 |
| Cetuximab by CXCR1 expression | 1.802 | 0.019 | 1.101 | 2.949 |
| Cetuximab by KRAS mutational status | 0.346 | 0.053 | 0.118 | 1.015 |

FIGURE 3

Table 3. Multivariate logistic regression for response at any time

|  | Odds ratio | P | 95% C.I. for odds ratio | |
|---|---|---|---|---|
|  |  |  | Lower | Upper |
| Tumour epithelial CXCR1 expression | 0.684 | 0.027 | 0.489 | 0.958 |
| Cetuximab by CXCR1 | 1.576 | 0.050 | 1.000 | 2.482 |
| Cetuximab by KRAS mutational status | 0.420 | 0.099 | 0.150 | 1.178 |

FIGURE 4

Table 4. Univariate survival analysis

| | Hazard ratio | P | 95% C.I. for hazard ratio | |
|---|---|---|---|---|
| | | | Lower | Upper |
| Treatment arm | 0.776 | 0.437 | 0.410 | 1.470 |
| Age | 1.027 | 0.058 | 0.999 | 1.055 |
| Tumour epithelial CXCR1 expression | 1.132 | 0.259 | 0.912 | 1.405 |
| Inflammatory infiltrate CXCL8 expression | 0.763 | 0.285 | 0.465 | 1.252 |
| Cetuximab by CXCR1 | 0.652 | 0.007 | 0.479 | 0.887 |
| KRAS | 1.426 | 0.305 | 0.724 | 2.811 |
| Cetuximab by KRAS | 1.180 | 0.746 | 0.433 | 3.220 |

FIGURE 5

Table 5. Multivariate survival analysis

| | Hazard ratio | P | 95% C.I. for hazard ratio | |
|---|---|---|---|---|
| | | | Lower | Upper |
| Age | 1.026 | 0.055 | 0.999 | 1.053 |
| Cetuximab by CXCR1 | 0.885 | 0.019 | 0.799 | 0.980 |

FIGURE 7

Table 6. Prognostic impact of CXCR1 in Cetuximab-treated patients

| CXCR1 expression | No of events | Median OS (months) | 95% Confidence Interval | |
|---|---|---|---|---|
| | | | Lower Bound | Upper Bound |
| Low (n=18) | 16 | 7.967 | 5.680 | 10.253 |
| High (n=29) | 24 | 19.033 | 10.272 | 27.795 |
| Overall (n=47) | 40 | 12.133 | 8.931 | 15.336 |

Log rank test: P=0.001

FIGURE 9

Table 7. Prognostic impact in non-Cetuximab treated patients

| CXCR1 expression | No of events | Median OS (months) | 95% Confidence Interval ||
|---|---|---|---|---|
| | | | Lower Bound | Upper Bound |
| Low (n=35) | 28 | 10.333 | 8.907 | 11.759 |
| High (n=27) | 21 | 10.733 | 7.793 | 13.674 |
| Overall (n=62) | 49 | 10.600 | 9.274 | 11.926 |
| Log rank test: P=0.739 |||||

FIGURE 11

Table 8. Role of high CXCR1 expression as predictive marker of response to Cetuximab treatment

| Treatment arm | No of events | Median OS (months) | 95% Confidence Interval ||
|---|---|---|---|---|
| | | | Lower Bound | Upper Bound |
| No Cetuximab (n=22) | 17 | 10.733 | 5.848 | 15.619 |
| Cetuximab (n=33) | 28 | 18.033 | 10.212 | 25.855 |
| Overall | 45 | 13.867 | 11.763 | 15.970 |
| Log rank test: P=0.013 |||||

FIGURE 13

Table 9. Patient response data to treatment in patients with low CXCR1 expression

| Treatment arm | No of events | Median OS (months) | 95% Confidence Interval | |
|---|---|---|---|---|
| | | | Lower Bound | Upper Bound |
| No Cetuximab (n=20) | 14 | 10.500 | 7.078 | 13.922 |
| Cetuximab (n=18) | 16 | 7.967 | 5.680 | 10.253 |
| Overall | 30 | 9.600 | 6.648 | 12.552 |
| Log rank test: P=0.140 | | | | |

SEQUENCE LISTING

<160> NUMBER OF SEQ ID NOS: 2

<210> SEQ ID NO 1
<211> LENGTH: 2502
<212> TYPE: DNA
<213> ORGANISM: Homo sapiens

<400> SEQUENCE: 1

```
tattcatcaa gtgccctcta gctgttaagt cactctgatc tctgactgca gctcctactg      60
ttggacacac ctggccggtg cttcagttag atcaaaccat tgctgaaact gaagaggaca     120
tgtcaaatat tacagatcca cagatgtggg attttgatga tctaaatttc actggcatgc     180
cacctgcaga tgaagattac agcccctgta tgctagaaac tgagacactc aacaagtatg     240
ttgtgatcat cgcctatgcc ctagtgttcc tgctgagcct gctgggaaac tccctggtga     300
tgctggtcat cttatacagc agggtcggcc gctccgtcac tgatgtctac ctgctgaacc     360
tggccttggc cgacctactc tttgccctga ccttgcccat ctgggccgcc tccaaggtga     420
atggctggat ttttggcaca ttcctgtgca aggtggtctc actcctgaag gaagtcaact     480
tctacagtgg catcctgctg ttggcctgca tcagtgtgga ccgttacctg gccattgtcc     540
atgccacacg cactgacc cagaagcgtc acttggtcaa gtttgtttgt cttggctgct     600
ggggactgtc tatgaatctg tccctgccct tcttccttt ccgccaggct taccatccaa     660
acaattccag tccagtttgc tatgaggtcc tgggaaatga cacagcaaaa tggcggatgg     720
tgttgcggat cctgcctcac acctttggct tcatcgtgcc gctgtttgtc atgctgttct     780
gctatggatt caccctgcgt acactgttta aggcccacat ggggcagaag caccgagcca     840
tgagggtcat ctttgctgtc gtcctcatct tcctgctttg ctggctgccc tacaacctgg     900
tcctgctggc agacaccctc atgaggaccc aggtgatcca ggagagctgt gagcgccgca     960
acaacatcgg ccgggccctg atgccactg agattctggg atttctccat agctgcctca    1020
accccatcat ctacgccttc atcggccaaa atttcgcca tggattcctc aagatcctgg    1080
ctatgcatgg cctggtcagc aaggagttct tggcacgtca tcgtgttacc tcctacactt    1140
cttcgtctgt caatgtctct tccaacctct gaaaaccatc gatgaaggaa tatctcttct    1200
cagaaggaaa gaataaccaa caccctgagg ttgtgtgtgg aaggtgatct ggctctggac    1260
aggcactatc tgggttttgg ggggacgcta taggatgtgg ggaagttagg aactggtgtc    1320
ttcaggggcc acaccaacct tctgaggagc tgttgaggta cctccaagga ccggcctttg    1380
cacctccatg gaaacgaagc accatcattc ccgttgaacg tcacatcttt aacccactaa    1440
ctggctaatt agcatggcca catctgagcc ccgaatctga cattagatga gagaacaggg    1500
ctgaagctgt gtcctcatga gggctggatg ctctcgttga ccctcacagg agcatctcct    1560
caactctgag tgttaagcgt tgagccacca agctggtggc tctgtgtgct ctgatccgag    1620 ctcaggggggg tggttttccc atctcaggtg tgttgcagtg tctgctggag acattgaggc    1680
aggcactgcc aaaacatcaa cctgccagct ggccttgtga ggagctggaa acacatgttc    1740
cccttggggg tggtggatga acaaagagaa gagggtttg gaagccagat ctatgccaca    1800
agaaccccct ttaccccat gaccaacatc gcagacacat gtgctggcca cctgctgagc    1860
cccaagtgga acgagacaag cagcccttag cccttcccct ctgcagcttc caggctggcg    1920
tgcagcatca gcatccctag aaagccatgt gcagccacca gtccattggg caggcagatg    1980
ttcctaataa agcttctgtt ccgtgcttgt ccctgtggaa gtatcttggt tgtgacagag    2040
tcaagggtgt gtgcagcatt gttggctgtt cctgcagtag aatggggca gcacctccta    2100 agaaggcacc tctctgggtt gaagggcagt gttccctggg gctttaactc ctgctagaac    2160
agtctcttga ggcacagaaa ctcctgttca tgcccatacc cctggccaag gaagatccct    2220
ttgtccacaa gtaaaggaa atgctcctcc agggagtctc agcttcaccc tgaggtgagc    2280
atcatcttct gggttaggcc ttgcctaggc atagccctgc ctcaagctat gtgagctcac    2340
```

-continued

```
cagtccctcc ccaaatgctt tccatgagtt gcagtttttt cctagtctgt tttccctcct    2400
tggagacagg gccctgtcgg tttattcact gtatgtcctt ggtgcctgga gcctactaaa    2460
tgctcaataa ataatgatca caggaaaaaa aaaaaaaaa aa                        2502
```

<210> SEQ ID NO 2
<211> LENGTH: 350
<212> TYPE: PRT
<213> ORGANISM: Homo sapiens

<400> SEQUENCE: 2

```
Met Ser Asn Ile Thr Asp Pro Gln Met Trp Asp Phe Asp Asp Leu Asn
1               5                   10                  15

Phe Thr Gly Met Pro Pro Ala Asp Glu Asp Tyr Ser Pro Cys Met Leu
            20                  25                  30

Glu Thr Glu Thr Leu Asn Lys Tyr Val Val Ile Ala Tyr Ala Leu
        35                  40                  45

Val Phe Leu Leu Ser Leu Leu Gly Asn Ser Leu Val Met Leu Val Ile
    50                  55                  60

Leu Tyr Ser Arg Val Gly Arg Ser Val Thr Asp Val Tyr Leu Leu Asn
65                  70                  75                  80

Leu Ala Leu Ala Asp Leu Leu Phe Ala Leu Thr Leu Pro Ile Trp Ala
                85                  90                  95

Ala Ser Lys Val Asn Gly Trp Ile Phe Gly Thr Phe Leu Cys Lys Val
            100                 105                 110

Val Ser Leu Leu Lys Glu Val Asn Phe Tyr Ser Gly Ile Leu Leu Leu
        115                 120                 125

Ala Cys Ile Ser Val Asp Arg Tyr Leu Ala Ile Val His Ala Thr Arg
    130                 135                 140

Thr Leu Thr Gln Lys Arg His Leu Val Lys Phe Val Cys Leu Gly Cys
145                 150                 155                 160

Trp Gly Leu Ser Met Asn Leu Ser Leu Pro Phe Phe Leu Phe Arg Gln
                165                 170                 175

Ala Tyr His Pro Asn Asn Ser Ser Pro Val Cys Tyr Glu Val Leu Gly
            180                 185                 190

Asn Asp Thr Ala Lys Trp Arg Met Val Leu Arg Ile Leu Pro His Thr
        195                 200                 205

Phe Gly Phe Ile Val Pro Leu Phe Val Met Leu Phe Cys Tyr Gly Phe
    210                 215                 220

Thr Leu Arg Thr Leu Phe Lys Ala His Met Gly Gln Lys His Arg Ala
225                 230                 235                 240

Met Arg Val Ile Phe Ala Val Val Leu Ile Phe Leu Leu Cys Trp Leu
                245                 250                 255

Pro Tyr Asn Leu Val Leu Leu Ala Asp Thr Leu Met Arg Thr Gln Val
            260                 265                 270

Ile Gln Glu Ser Cys Glu Arg Arg Asn Asn Ile Gly Arg Ala Leu Asp
        275                 280                 285

Ala Thr Glu Ile Leu Gly Phe Leu His Ser Cys Leu Asn Pro Ile Ile
    290                 295                 300

Tyr Ala Phe Ile Gly Gln Asn Phe Arg His Gly Phe Leu Lys Ile Leu
305                 310                 315                 320
```

```
Ala Met His Gly Leu Val Ser Lys Glu Phe Leu Ala Arg His Arg Val
                325                 330                 335

Thr Ser Tyr Thr Ser Ser Ser Val Asn Val Ser Ser Asn Leu
            340                 345                 350
```

CXCR1 AS A PREDICTOR OF RESPONSE TO TREATMENT WITH EPIDERMAL GROWTH FACTOR RECEPTOR THERAPEUTIC

FIELD OF THE INVENTION

The present invention is concerned with the determination of a molecular marker for use in the prediction of those subjects afflicted by cancer that would benefit from treatment with an Epidermal Growth Factor Receptor (EGFR) targeted therapeutic, specifically but not limited to Cetuximab and Panitumumab. This provides for a method of characterising a tumour to indicate if this tumour will respond to treatment with an EGFR inhibitor and stratifying a subject with a tumour, as a subject who would or would not respond to the treatment with an EGFR inhibitor accordingly.

BACKGROUND OF INVENTION

The Epidermal Growth Factor Receptor (EGFR) and its downstream signaling pathways, primarily the mitogen-activated protein kinase (MAPK) and the phosphatidylinositol-3 kinase (PI3K)/Akt pathways, are known to play a significant role in tumour growth and progression. Over-expression of the EGFR has been identified in numerous solid tumours including colon, rectal, lung, ovarian, and head and neck cancers. Many clinical studies have indicated that over-expression of EGFR in these tumours is associated with poor prognosis, and shorter overall survival of subjects afflicted with cancer.

As EGFR signalling appears to have limited relevant physiological function in an adult, provision of inhibitors of EGFR signalling is believed to allow selective targeting of malignant cells in a subject afflicted by cancer, whilst only causing limited toxicity to normal cells. EGFR has become a widely studied molecular target and major pharmaceutical companies have developed either small molecule inhibitors to EGFR such as Gefitinib (Astrazeneca) and Tarceva (OSI) or antibodies that exhibit high affinity binding and inhibit ligand-induced activation of the EGFR, such as Cetuximab (Eli Lilly/BMS/Merck Serono) and Panitumimab (Amgen).

Clinical trials of these EGFR targeted therapeutics have indicated that only subsets of patients actually derive clinical benefit from the provision of EGFR-targeted therapeutics. EGFR is expressed in 30-85% of colorectal cancers and its expression level has been linked to reduced survival. Trials conducted in patients with metastatic colorectal cancer have reported favourable response rates in only 23% of patients, even when the EGFR-therapeutic is combined with chemotherapy, and significantly lower response rates of only 11% when the EGFR-therapeutic in used as monotherapy (Saltz et al. J Clin Oncol 2004;22:1201-1208; Cunningham et al., N Engl J Med 2004;351:337-345). Identifying which patients respond favourably to the provision of EGFR-therapeutics has thus been a subject of intense research. Importantly, such predictive biomarkers of patient response to EGFR-therapeutics hold the promise to not only improve treatment outcomes for specific patients, but also will enable the full promise of these molecular-targeted therapeutic agents be realized.

Several early candidates were proposed to serve as predictive biomarkers of response to EGFR-therapeutics, including the expression level of the EGFR itself. Investigations in metastatic colorectal cancer however failed to demonstrate a correlation between EGFR expression as measured by immunohistochemistry and the clinical response to Cetuximab in combination with irinotecan chemotherapy (Chung et al, J Clin Oncol. 2005;23:1803-1810). Alternatively, while the use of activating mutations in the kinase domain of the EGFR have been successful to predict response to the provision of small molecule agents targeting the kinase domain of the receptor, these mutations are unable to predict response to antibodies such as Cetuximab that bind to the ectodomain of the receptor. Furthermore, mutation rates of the EGFR in certain diseases including colorectal cancer are low, and in diseases where mutations of the EGFR are present, these represent only small populations of the entire patient population (typically <10%) (Janne et al. J Clin Oncol 2005;23:3227-3234).

More recent attention has focused on identifying mutations resident within the constituent proteins of the signal transduction pathways that are activated by the EGFR. Following a number of Phase III clinical trials conducted in advanced stage colorectal cancer disease, Cetuximab has been approved for the treatment of subjects with epidermal growth factor receptor (EGFR)-expressing, KRAS wild-type metastatic, colorectal cancer (mCRC), in combination with chemotherapy, on the basis that tumours that do not harbour mutations are more likely to respond to EGFR-targeted treatment strategies. However, larger trials that have enrolled significantly larger numbers of patients have subsequently reported that use of KRAS status does not clearly predict response to EGFR therapeutics. For example, the randomized phase III COIN study, in which greater than 2500 patients took part, failed to observe any benefit from the addition of Cetuximab to oxaliplatin-based chemotherapy in first-line treatment of patients with advanced colorectal cancer. While the study showed that Cetuximab increased the response rate measured at 12 weeks after therapy, there was no evidence of benefit in terms of progression-free survival or overall survival in KRAS wild-type patients or even in patients selected by additional mutational analysis of their tumours (Maughan et al., Lancet Oncol 2011;377:2103-2114). Therefore additional biomarkers are required to accurately select patients and differentiate responsive from non-responsive subjects.

Given the intention in the provision of therapy or use of a therapeutic agent to improve clinical outcome through a beneficial response, it would be advantageous to provide a diagnostic test that identifies responsive subjects to the therapy/therapeutic agent being considered. This is particularly advantageous to identify those subjects who are unlikely to benefit and are therefore unnecessarily exposed to toxic side effects of therapeutic agents. Further, it is advantageous to minimise the likelihood of unnecessary expense being incurred through treatment of subjects with therapy/therapeutic agents that are unlikely to provide benefit, and/or minimise the delay in a subject being treated with an alternative drug(s) which might prove more beneficial.

SUMMARY OF INVENTION

The inventors have determined that the expression level of CXCR1 in a tumour of a cancer subject can be indicative of beneficial drug response and survival of a cancer subject treated with an EGFR inhibitor. In particular, the inventors have identified CXCR1 as a predictive biomarker to identify or predict those subjects who will benefit from treatment with the EGFR-targeted therapeutic Cetuximab (or other agents including Panitumumab) and in particular those colorectal cancer subjects who will benefit from the addition of EGFR-targeted therapeutics to cytotoxic (e.g. oxaliplatin-based) chemotherapy.

Accordingly a first aspect of the invention provides the use of CXCR1 as a biomarker in a method of predicting response in a subject to treatment with an Epidermal Growth Factor Receptor therapeutic, in particular an EGFR inhibitor, wherein an expression level of CXCR1 in a tumour sample of a cancer subject increased from that of the expression level of CXCR1 in a Control is indicative the subject will respond to treatment with the EGFR therapeutic.

Although prior studies in the literature suggest that ligand-induced activation of G-protein coupled receptors can induce an intracellular transactivation of growth factor receptors, including the EGFR receptor, ((Venkatakrishnan et al, J Biol Chem 2000;275:6868-6875) and (Kyriakis et al. J Leukocye Biol 2011; 90:929-939)) and transactivation of the EGFR has been indicated to constitute an important aspect of interleukin-8 signaling underpining many cellular responses including proliferation and survival (Waugh and Wilson, Clin Cancer Res 2008; 14; 6735-6741) and (Itoh et al, Cytokine 2005;29:275-282), to date biomarkers for EGFR targeted therapeutics have been largely determined by considering the levels of response indicator genes following treatment with an EGFR targeted therapeutic in responding and non-responding subjects.

In contrast, whilst not wishing to be bound by theory, the present inventors have determined tumour sensitivity to EGFR-therapeutics can be predicted based on the tumour having robust EGFR signaling, wherein such a tumour becomes "addicted" to the EGFR signaling pathway, and is hyper-sensitive to the loss of EGFR signalling, wherein dependence of the tumour on the EGFR signaling pathway for proliferation and survival can be detected by considering whether a tumour is CXCR1 enriched relative to tumors from non-responding subjects.

In embodiments, it is considered the IL8 receptor CXCR1 is as an independent predictor of therapeutic response to EGFR-targeted therapeutics in metastatic colorectal cancer subjects.

In embodiments the method can comprise the steps: determining in a tumour sample from a cancer subject the expression level of CXCR1; comparing the determined expression level of CXCR1 against the expression level of CXCR1 in a Control, for example from tumours of a control population, where the tumours of the Control population may be tumours of the same tissue as the tumour of the subject, and may be of equivalent stage and grade as the tumour of the subject, wherein when the expression level of CXCR1 determined in the subject is determined to be increased above the expression level of the Control, for example the median expression level within a control population, it is indicative that the cancer subject would benefit from treatment with an EGFR modulator/Epidermal Growth Factor Receptor therapeutic. In embodiments the method can comprise the steps of: determining the expression level of CXCR1 in a tumour sample of a tumor from a subject, comparing the determined level with the expression level of CXCR1 in a control sample wherein when the expression level of CXCR1 in the tumour from the subject is greater than the expression level of CXCR1, suitably the median expression level of CXCR1 characterised in a control sample of the respective cancer or tumour tissue, the tumour is determined as EGFR inhibitor sensitive and the subject will likely respond to treatment with an EGFR inhibitor. In embodiments, the control sample can be generated determined on the expression level determined in a control population. In embodiments, a control sample can be from a tumour representative of a median expression level of CXCR1 in tumours of the same tissue type, more suitably of the same stage and grade, as that of the subject. Suitably the control sample may be synthetically or artificially provided based on results from tumour representative of a median expression level of CXCR1 in tumours of the same tissue type as that of the subject.

Suitably when the expression level of CXCR1 of a tumour of the subject is increased with respect to a Control CXCR1 expression level of a sample tumour, preferably the median expression level of CXCR1 of the Control, the tumour may be characterised as EGFR inhibitor sensitive and the subject will likely beneficially respond therapeutically to treatment with an EGFR inhibitor and thus be classified as a responder.

In embodiments the method is an in vitro method wherein the step of determining the expression level of CXCR1 can comprise taking a biological sample from the subject and then measuring the expression level of CXCR1 in the sample. In embodiments a tumour sample can be a tissue sample comprising cancer cells from the cancer subject. For example, a tumour sample can be obtained from a subject prior to and after exposure of the cancer cells to an EGFR targeted therapeutic or other chemotherapeutic agent. In embodiments the tumour sample can be an ex vivo tumour cell. The tumour sample can be, for example, a tissue sample comprising cancer cells wherein the tissue sample is frozen, fixed, paraffin embedded, or fresh. The tissue may be from a biopsy. The term also encompasses cells that are the progeny of a subject's tumour, e.g. cell culture samples derived from a primary tumour or samples comprising cells, protein or nucleic acid shed from a tumour.

In embodiments of the invention, the method can include the step of analysing a circulating tumour cell or tissue sample from a subject's tumour, including, but not limited to, the use of a diagnostic tissue sample obtained from the subject at the time of presentation for expression of the biomarker. The step of analysing may include traditional immunohistochemistry-based analysis to determine the expression of the defined predictive biomarker CXCR1 as discussed herein. In embodiments, determining an expression level of a CXCR1 above or increased with respect to the expression level of a Control, indicative that a cancer subject would benefit from treatment with an EGFR targeted therapeutic, can comprise the steps of;

analysing a tissue sample from a cancer subject's tumour, or cells from a subject's tumour including the analysis of circulating tumour cells from the blood or other bodily sample taken from the subject, determining the expression level of the biomarker CXCR1, determining whether the level of the biomarker is greater than that of a Control, wherein an expression level of the biomarker above the Control is indicative the subject will gain clinical benefit (beneficially respond) from the provision of an EGFR therapeutic. In embodiments a Control can be a median expression level of CXCR1 of a cancer population with tumours of the same tissue type, preferably the same stage and/or grade as the tumour from the subject.

Subject

As will be appreciated, the method provides for the identification of a subgroup of cancer subjects (responders) who will benefit from treatment with an EGFR targeted therapeutic, in particular an EGFR inhibitor. Accordingly, an EGFR inhibitor, in particular cetuximab or panitumumab, may be provided to a subject for use in the treatment of a tumour in the subject wherein a tumour sample from said tumour has been identified to have an expression level of the CXCR1 biomarker that is above or increased with respect to a level in a Control tumour sample. Also provided is the use of an EGFR inhibitor, in particular cetuximab or panitumumab, in the manufacture of a medicament for the treatment of a subject with cancer, wherein a tumour from said cancer has been identified to have an expression level of CXCR1 above the expression level of a control tumour sample. Further provided is a method of treating a subject with a tumour wherein the expression level of CXCR1 in the tumour is greater than the expression level of CXCR1 in a Control, wherein the method comprises administering an EGFR inhibitor to the subject. In embodiments a subject may have been previously treated with or will be receiving chemotherapy or radiotherapy including standard conformal radiotherapy, intensity-modulated radiotherapy or cyberknife radiotherapy. In embodiments the cells from a cancer subject's tumour can have been subjected to chemotherapy prior to the assay method. In embodiments, patients with colorectal cancer may have previously been subjected to treatment with oxaliplatin, irinotecan or fluoropyrimidine therapy prior to the assay method.

In embodiments the cancer subject can be a candidate for treatment with Gefitinib (Astrazeneca), Tarceva (OSI), Cetuximab (Merck Serono), Panitumimab (Amgen) or any other anti EGFR drugs or for the screening of drugs for anti EGFR activity. In embodiments the cancer subject can be a candidate for treatment with Cetuximab (Merck Serono) or Panitumimab (Amgen). In an embodiment the cancer subject can be a candidate for treatment with Cetuximab (Merck Serono).

The EGFR therapeutic agent may exhibit differential degrees of selectivity or specificity to members of the extended EGFR-family of receptors including ErbB2, ErbB3 and ErbB4. In particular embodiments, treatment with an EGFR inhibitor is by treatment with Cetuximab or panitumumab, more particularly treatment with Cetuximab.

Tumour

The tumour or cancer may be selected from colorectal cancer, preferably metastatic colorectal cancer, colorectal tumours, NSCLC tumours, head and neck tumours and ovarian tumours. In embodiments the cancer subject can have a solid tumour, for example, within the colon, lungs, ovaries, colon or gastro-intestinal tract, or head and neck. In embodiments the cancer subject can have colon cancer, rectal cancer, lung cancer, ovarian cancer, gastro-oesophageal cancer and head and neck cancer. In embodiments the cancer subject can have a primary tumour within the colon, rectum, gastro-oesphageal tract, ovaries or head and neck, with secondary metastatic lesions disseminated to other tissues within the body. In embodiments, where the cancer is pathologically confirmed as colorectal cancer, the use of CXCR1 as a predictive biomarker may be used in relation to any subject being considered for treatment with an EGFR inhibitor in the adjuvant or metastatic disease setting, as would be the case for performing a Ras-mutation analysis currently. Alternatively, the use of CXCR1 as a biomarker to indicate those subjects that will respond to treatment with an EGFR therapeutic may also be used to guide the provision of an EGFR inhibitor in patients with solid tumours classified as non-small cell lung cancer (NSCLC), head and neck cancer, and ovarian cancer etc.

Representative nucleic acid sequences and amino acid sequences for CXCR1 are provided in the sequence listing at the end of the specification. As will be appreciated, nucleic acid or amino acid variants of these sequences exist and are encompassed by the present application.

The expression level of the CXCR1 biomarker in a Control may be set at the mean, mode or preferably the median level of expression (median expression level) or further defined value as observed across a spectrum of respective cancer tissue, for example colorectal cancer tissue. In embodiments the expression level of the CXCR1 biomarker in a Control can be the expression level, suitably the mean, mode or preferably median expression level, as determined in tumours of the same tissue type as that of the tumour of the subject being tested. In embodiments the expression level of the of the CXCR1 biomarker in a Control can be the expression level, suitably the mean, mode or prefereably median expression level as determined in tumours of the same tissue type and equivalent stage and grade as that of the tumour of the subject being tested. This provides a normalised expression level and the normalised expression level can be used to determine an increased expression level which is indicative that beneficial response will be observed when an EGFR inhibitor is administered to the subject. Additionally, reference expression levels to define the normal range of expression of the biomarker in a tumour(s) may be provided by considering a sub population of cancer subjects, for example subjects suffering from invasive tumours, an age range of subjects, the gender of subjects, or a selection of subjects based on expression of another biomarker. As will be appreciated, the determination of the subjects from which samples may be provided can typically be made in view of the subjects to be studied, or tumours to be assessed/classified as responder/non-responder. In embodiments, the expression level of CXCR1 in a tumour can be considered relative to the cellular location of the expression and corresponding expression at that cellular location in the control, for example the expression level of CXCR1 may be localized to the cell-membrane, the cytoplasmic compartment of the cell, the nuclear and perinuclear zones of the cell or be resident within exosomal bodies within or out-with the tumour mass.

By "above, increased or greater than" is meant expression levels of the biomarker determined in the sample above the normalised expression level of the biomarker in a Control or a level of biomarker that has been correlated with an increased likelihood the subject will exhibit a beneficial response to an EGFR inhibitor cancer therapy. A likelihood score which is indicative of the likelihood of beneficial response to EGFR inhibitor treatment may be determined using weighted values based on an expression level of CXCR1 and the contribution to response to EGFR inhibitor cancer therapy based on the level of CXCR1. It is contemplated that an incremental increase in the level of, for example CXCR1 above a Control, may provide for an incremental increase in clinical outcome to provision of an EGFR-targeting therapeutic. By "beneficial response" is meant a favourable subject response to a drug as opposed to an unfavourable response. Favourable subject response may be assessed by determining one or more of the loss of detectable tumour, decrease in tumour size, decrease in tumour number, tumour growth arrest, enhancement of anti-tumour immune response, regression or rejection of the tumour, relief to some extent of one or more symptoms associated with the tumour, and/or an increase in the length of survival following treatment.

As will be appreciated, the methods of the invention may further comprise the step of designing a treatment regimen for a subject. For example, an anti-EGFR antibody may be administered to those subjects including a tumour which has increased (or above-median) expression of CXCR1. In contrast to this, other drug regimens, for example chemotherapeutic therapies, could be administered to a subject with a tumour which has a decreased expression level of CXCR1.

In embodiments, the Control expression level can be as provided in the examples discussed herein. As will be understood, the Control expression level can be generated for specific cancer types, or specific subtypes of subjects based on age or the like to allow for the comparison of the expression level detected or measured from the subject's tumour.

Determining the Expression Level

In embodiments, determining the expression level can comprise as least one of determining the expression of CXCR1 protein in a tumour or tumour-derived sample taken from the subject determining the amount of mRNA encoding CXCR1 in a tumour or tumour-derived sample taken from the subject, determining the copy number of CXCR1 in a tumour or tumour-derived sample taken from the subject, determining and characterizing the expression of any non-coding or coding polymorphism within the nucleotide sequences encoding CXCR1 in a tumour, tumour-derived or non-tumour tissue sample taken from the subject.

Suitably an increased copy number is indicative that administration of an EGFR inhibitor will provide a beneficial response to a subject. By copy number is meant the number of discrete instances of a gene encoding for a biomarker as indicated as present in a tumour sample when compared to a reference sample. Normal copy number would be defined as the normal copy of the gene determined in healthy subjects and healthy tissue specimens. The reference sample may be provided from a sub-population of cancer subjects or an appropriately matched cohort of normal patients. Copy number may be determined by methods as will be known in the art. Exemplary methods include, but are not limited to, hybridisation-based assays, amplification-based assays and gene transcription or protein expression assays.

Suitably, any one of the determinations of expression level of the biomarker, CXCR1, may be used in combination in the methods of the invention.

Methods for determining the amount of biomarker polypeptide CXCR1 or the amount of mRNA encoding biomarker CXCR1 in a sample are disclosed herein and would generally be known to those of skill in the art. In embodiments, determining the level of expression of biomarker polypeptide, CXCR1, may comprise determining the level of activity of the receptor, and/or determining the level of interaction between the biomarker (CXCR1) and a binding partner (e.g., IL-8 or GCP-2).

In embodiments of the methods of the invention the expression level can be measured by determining the mRNA level of the CXCR1 biomarker (measured, for example using reverse-transcriptase polymerase chain reaction (RT-PCR), quantitative RT-PCR methodology or other PCR methodologies, Northern blot, in-situ hybridisation, dot-blot, Taqman, RNAse protection assay or using array hybridisation, for example microarray). In such embodiments, probes of nucleic acid molecules that can hybridise to mRNA of the biomarker CXCR1, under stringent conditions can be used to identify the expression level of the biomarker CXCR1. PCR methods to allow for amplification of nucleic acid to allow determination of the level of expression are well known. Rules for designing PCR primers are now established in the art.

These methods can include chip based technologies for the detection and/or quantification of nucleic acid. In such methods, microarrays may be used wherein polynucleotide sequences of interest are arrayed on a substrate. These can include oligonucleotide microarrays or cDNA microarrays comprising one or more of the biomarkers that correlate with sensitivity to an EGFR inhibitor. The arrayed sequences are then contacted under conditions suitable for specific hybridization with detectably labelled cDNA generated from mRNA of a test sample. The mRNA is typically total RNA isolated from a tumour sample. Based on the gene expression profile of a tumour sample from a cancer subject, for example from a tumour biopsy, it can be determined if the cells differ from control cells and if so whether they show a resistant or sensitive profile to the cancer treatment with an EGFR inhibitor.

Quantification of hybridization of each arrayed element allows for assessment of corresponding mRNA abundance. Microarray analysis may, for example, be performed using commercially available equipment, for example using Affymetrix GenChip® technology.

In another embodiment the expression level can be measured by determining the protein level of the CXCR1 biomarker (measured, for example, by immunohistochemistry proteomics techniques, for example using a commercially available CXCR1 monoclonal antibody, Enzyme Linked Immunosorbent assay (ELISA), 2-dimensional SDS PAGE, Western blot, Immunoprecipitation, fluorescence activated cell sorting (FACS) or flow cytometry). These methods can include membrane, solution or chip based technologies for the detection and/or quantification of CXCR1 protein.

Expression of the CXCR1 biomarker may be detected and measured using antibody-based approaches, wherein either polyclonal or monoclonal antibodies specific for the biomarker, CXCR1, can be used to detect tumour epithelial expression. Typically, an antibody which specifically binds to the biomarker as disclosed herein, for example CXCR1 provides a detection signal that results from specific binding to its target protein and that it does not detect other proteins in immunochemical assays and can immunoprecipitate CXCR1 from solution. Immunohistochemical determination of the level of a biomarker referenced herein, for example CXCR1, will be essentially qualitative. However, this can still allow prognostic grouping of a subject being tested as an EGFR modulator, for example inhibitor, responder or non responder.

Determination of the level of expression of at least one of CXCR1 may be qualitative (for example higher or lower than Control from considering for example immunohistochemical stained sample) or quantitative. In embodiments, optionally, the expression level of a biomarker can be at least two-fold, at least three-fold, at least four-fold or higher than that of a Control. In other embodiments, optionally, the expression level of a biomarker can be determined to be p-value <0.05 in Anova (t test) or other relevant statistical analysis.

In embodiments, the methods of the invention can be carried out in vitro, for example on samples obtained from a subject. In alternative embodiments, some methods of the invention may be practiced on data previously generated from a subject (for example from data generated from microarray data of a tumour sample) and thus do not require the direct use of a physical patient sample. For each aspect of the invention, the methods may include the further step of creating a report for a subject containing a summary of the expression levels of the biomarker CXCR1, in a tumour sample. In one aspect this report is an electronic form.

In embodiments the use of the biomarker described in the invention CXCR1 may be used in tandem with other defined biomarkers. In embodiments at least one biomarker used in these protocols includes CXCR1 or fragments thereof which provide for determination of CXCR1 expression or activity in a cell. In embodiments at least one biomarker is selected from CXCR1.

In embodiments, the use of CXCR1 as a biomarker, can be used alone or in combination with other biomarkers as a predictive test or means to select subjects that will likely respond beneficially to administration of an EGFR targeted therapeutic, for example an EGFR inhibitor, in combination with oxaliplatin-based chemotherapy as a treatment for stage IV or metastatic colorectal cancer, administration of an EGFR targeted therapeutic, for example an EGFR inhibitor, in combination with irinotecan based chemotherapy as treatment for stage IV or metastatic colorectal cancer, administration of an EGFR targeted therapeutic, for example an EGFR inhibitor, in combination with fluoropyrimidine based chemotherapy as a treatment for stage IV or metastatic colorectal cancer, or administration of an EGFR targeted therapeutic, for example an EGFR inhibitor, in combination with another approved cancer chemotherapeutic agent as an adjuvant based post surgical treatment for subjects diagnosed with early stage (stage II/III) colorectal cancer including but not limited to a combination of oxaliplatinum, irinotecan and/or fluoropyrimidine-based chemotherapy.

In embodiments, the results of the methods of the invention can be communicated to parties including a physician, a researcher or a subject for use in determining further treatment options. In embodiments the results can be provided in a form which are transmittable to such parties. The results may be provided in a tangible form such as paper, computer readable media or the like or on an intangible medium, for example an electronic signal, email, or via a website. Alternatively, the results may be recorded in a sound and transmitted through a suitable medium such as digital cable lines, fiber optic cables, wireless or the like. Accordingly, the methods can encompass a method of producing a transmittable form of a result of the expression level of a biomarker, preferably CXCR1 in a tumour sample.

In a further aspect there is provided a method to determine the likelihood that a cancer subject will respond therapeutically to a cancer treatment wherein the method comprises a) measuring the expression level of the CXCR1 biomarker in a biological sample from the cancer subject, b) exposing the biological sample to a cancer treatment that includes an EGFR targeted therapeutic, c) following the step b) of exposing the biological sample to the cancer treatment, measuring the expression level of CXCR1 as an indicator of the response of the tumour or tumour-derived sample and comparing the expression level of CXCR1 as an indicator of the response of the tumour or tumour-derived sample to that of the expression level of the CXCR1 biomarker in a biological sample from the cancer subject at step a).

In embodiments, measuring the expression level of CXCR1 may include the assessment of a cellular or molecular readout, so that the analysis predicts an increased likelihood that the cancer subject will respond beneficially to an EGFR modulator.

In embodiments the method enables the identification and/or selection of patients to receive an EGEF targeted therapeutic, for example Cetuximab, for the treatment of cancer, in particular any-stage of colorectal cancer. In embodiments the method can enable the selection of cancer subjects to receive an EGFR targeted therapeutic, for example Cetuximab, for stage II colorectal cancer following surgical resection. In embodiments, the patients may receive Cetuximab as a monotherapy or as a component of adjuvant-treatment.

The methods of the invention may be used to provide screening assays to determine whether a subject is susceptible or resistant to treatment with one or more EGFR modulators/EGFR targeted therapeutics. The methods of the invention may be used to monitor the treatment of a subject having cancer, wherein the cancer is treated by administering one or more EGFR modulators/EGFR targeted therapeutics. The CXCR1 biomarker can be used to monitor the progress of disease treatment in those subjects undergoing treatment to determine if there is a change in the sensitivity of the tumour to treatment with and EFGR modulator/EGFR targeted therapeutic. The methods of the invention may be used to provide genetic profiles of cancer subjects which can enable treatment strategies to be provided to a specific subject.

Kits

The invention also provides kits for determining or predicting whether a subject is susceptible to a cancer treatment.

In one aspect there is provided a kit for use in a method of the invention comprising a container comprising one or more reagents for monitoring the expression level of CXCR1, and one or more EGFR modulators for use in testing cells from a cancer subject. In an embodiment, a reagent of the kit can be an antibody with binding specificity to the CXCR1 biomarker. In another embodiment the reagent of the kit can be a microarray to enable the level of mRNA of the biomarker CXCR1 to be determined. In another embodiment, the reagent of the kit can comprise a PCR probe with binding specificity to a mRNA of a biomarker CXCR1 to be determined. In embodiments, the kit can further comprise instructions for determining whether or not a cancer subject will respond therapeutically to a method of treating cancer, specifically a method of treating cancer comprising an EGFR inhibitor. In particular embodiments of the kit, the kit may further comprise antibodies with binding specificity to at least one additional biomarker, and/or PCR probes with binding specificity to at least one additional biomarker.

In embodiments, CXCR1 includes active forms of CXCR1 and active fragments thereof. In embodiments at least one biomarker can be selected from CXCR1 as indicated by SEQ ID NO:1 or SEQ ID NO:2. Other additional biomarkers may include CXCR2, CXCR4, CXCR7, CXCL12, CXCL1, CXCL5 or CXCL6.

In an embodiment, the kit can determine or predict whether a patient would be susceptible to respond to a cancer treatment comprising an EGFR inhibitor.

In all aspects of the present disclosure, there may be provided the further step of determining the expression level of at least one further biomarker. In embodiments, the methods may include determination of at least three biomarkers, at least four biomarkers, at least five biomarkers or more. In embodiments a further biomarker can be selected from other previously reported biomarkers including mutant EGFR, gain-of-function mutations in K-Ras, loss of PTEN and/or p53 functionality through mutation or diminished expression. The detection of mutated K-Ras is typically considered to be indicative that there will be a decreased likelihood of the cancer subject responding therapeutically to a method of treating cancer comprising administering an EGFR inhibitor. A biomarker may be used in an in vitro assay to predict in vivo outcome. In a further embodiment of the invention, the additional biomarkers may be novel/ newly-described biomarkers identified from genome-wide screens (e.g. microarray) or through hypothesis-driven research.

Preferred features and embodiments of each aspect of the invention are as for each of the other aspects mutatis mutandis unless context demands otherwise.

Definition of Terms

"Probes" may be derived from naturally occurring or recombinant single- or double stranded nucleic acids or may be chemically synthesised. Such probes may be labelled with reporter molecules. Nucleic acid probes may be used in Southern, Northern or in situ hybridizations to determine whether DNA or RNA encoding a biomarker is present within a cell type, tissue or organ. Probes can also be antibodies which have binding specificity to a biomarker.

"Reporter molecules" can be fluorescent, chemiluminescent, or chromogenic agents, radionuclides, and enzymes which are associated to a probe and allow the detection of the probe.

"Stringent conditions" refers to conditions that allow for hybridization of substantially related nucleic acid sequences. Stringent conditions, within the meaning of the invention are 65° C. in a buffer containing 1 mM EDTA, 0.5M NaHPO4 (pH7.2), 7% (w/v) SDS. For instance, such conditions will generally allow hybridization of sequence with at least 85% identity, preferably at least about 90% sequence identity, more preferably with at least 95% sequence identity. Hybridization conditions and probes can be adjusted in well characterised ways to achieve selective hybridization.

"Active", with respect to a CXCR1 polypeptide or other CXCR or CXCL polypeptides refers to those forms, fragments or domains of CXCR1 polypeptide which retain biological and/or antigenic activity of a CXCR or CXCL polypeptide.

"EGFR modulators or EGFR targeted therapeutics" as used herein is intended to mean a compound or drug, for example a biological molecule or small molecule that directly or indirectly modulates the EFGR signal transduction pathway. EGFR modulators or EGFR targeted therapeutics can include EGFR specific ligands, small molecule EGFR inhibitors, EGFR monoclonal antibodies and chimeric versions of such antibodies. EGFR modulators or EGFR targeted therapeutics may include biological molecules or small molecules. Biological molecules may include all lipids and polymers of monosaccharides, amino acids and nucleotides having a molecular weight greater than 450 kDa. Thus biological molecules include, for example, oligosaccharides and polysaccharides; oligopeptides, polypeptides, peptides and proteins, and oligonucleotides and polynucleotides. Oligonucleotides and polynucleotides include for example DNA and RNA. Biological molecules further include derivatives of any of the molecules described above. For example, derivatives of biological molecules including lipid and glycosylation derivatives of oligopeptides, poplypeptides, peptides, and proteins. Derivatives of biological molecules further include lipid derivatives of oligosaccharides and polysaccharides e.g. lipopolysaccharides. Most typically, biological molecules are antibodies or functional equivalents of antibodies wherein the functional equivalents have binding characteristics comparable to those of antibodies and inhibit the growth of cells that express EGFR. Such functional equivalents can include chimeric, humanised, and single chain antibodies as well as fragments thereof. Functional equivalents of antibodies also include polypeptides with amino acid sequences substantially the same as the amino acid sequence of the variable or hypervariable regions of the antibodies, for example wherein the amino acid sequence differs from the other sequence by means of one or more substitutions, deletions and/or additions. Preferably less than 50%, more preferably less than 25%, more still more preferably less than 10% of the number of amino acids in a sequence are substituted, added and/or deleted from the protein.

In embodiments an EGFR antibody can be selected from the antibodies described in U.S. Pat. Nos. 6,235,883, 5,558,864, and 5,891,996. The EGFR antibody can be, for example, AGX-EGF (Amgen Inc.) (also known as panitumumab) which is a fully human IgG2 monoclonal antibody. The sequence and characterization of ABX-EGF, which was formerly known as clone E7.6.3, is disclosed in U.S. Pat. No. 6,235,883 at column 28, line 62 through column 29, line 36 and FIGS. 29-34, which is incorporated by reference herein. The EGFR antibody can also be, for example, EMD72000 (Merck KGaA), which is a humanized version of the murine EGFR antibody EMD 55900. The EGFR antibody can also be, for example: h-R3 (TheraCIM), which is a humanized EGFR monoclonal antibody; Y10 which is a murine monoclonal antibody raised against a murine homologue of the human EGFRvIII mutation; or MDX-447 (Medarex Inc.).

EGFR modulators or EGFR targeted therapeutics useful in the invention may also be small molecules. These can include a molecule that is not a biological molecule. Some examples of small molecules include organic compounds, organometallic compounds, salts of organic and organometallic compounds, saccharides, amino acids, and nucleotides. Small molecules further include molecules that would otherwise be considered biological molecules, except their molecular weight is not greater than 450 kDa. Thus, small molecules may be lipids, oligosaccharides, oligopeptides, and oligonucleotides and their derivatives, having a molecular weight of 450 kDa or less.

Small molecules include compounds that are found in nature as well as synthetic compounds. In one embodiment, the EGFR modulator is a small molecule that inhibits the growth of tumor cells that express EGFR. In another embodiment, the EGFR modulator is a small molecule that inhibits the growth of refractory tumor cells that express EGFR. ERESSA (ZD1939), which is a quinozaline derivative that functions as an ATP-mimetic to inhibit EGFR. See, U.S. Pat. No. 5,616,582; WO 96/33980 at page 4 is an example of a small molecule EGFR antagonist. Another example of a small molecule EGFR antagonist is TARCEVA (OSI-774), which is a 4-(substitutedphenylamino)quinozaline derivative [6,7-Bis(2-methoxy-ethoxy)-quinazolin-4-yl]-(3-ethynyl-1-phenyl)amine hydrochloride] EGFR inhibitor See WO 96/30347 (Pfizer Inc.) at, for example, page 2, line 12 through page 4, line 34 and page 19, lines 14-17. TARCEVA may function by inhibiting phosphorylation of EGFR and its downstream PI3/Akt and MAP (mitogen activated protein) kinase signal transduction pathways resulting in p27-mediated cell-cycle arrest. See Hidalgo et al., Abstract 281 presented at the 37th Annual Meeting of ASCO, San Francisco, Calif., 12-15 May 2001.

Other small molecules are also reported to inhibit EGFR, many of which are thought to be specific to the tyrosine kinase domain of an EGFR. Some examples of such small molecule EGFR antagonists are described in WO 91/116051, WO96/30347, WO96/33980, WO97/27199. WO97/30034, WO97/42187, WO97/49688, WO98/33798, WO00/18761, and WO00/31048. Examples of specific small molecule EGFR antagonists include C1-1033 (Pfizer Inc.), which is a quinozaline (N-[4-(3-chloro-4-fluoro-phenylamino)-7-(3-mprpholin-4-yl-propoxy)-quinazolin-6-yl]- acrylamide) inhibitor of tyrosine kinases, particularly EGFR and is described in WO00/31048 at page 8, lines 22-6; PKI166 (Novartis), which is a pyrrolopyrimidine inhibitor of EGFR and is described in WO97/27199 at pages 10-12; GW2016 (GlaxoSmithKline), which is an inhibitor of EGFR and HER2; EKB569 (Wyeth), which is reported to inhibit the growth of tumor cells that overexpress EGFR or HER2 in vitro and in vivo; AG-1478 (Tryphostin), which is a quinazoline small molecule that inhibits signaling from both EGFR and erbB-2; AG-1478 (Sugen), which is a bisubstrate inhibitor that also inhibits protein kinase CK2; PD 153035 (Parke-Davis) which is reported to inhibit EGFR kinase activity and tumor growth, induce apoptosis in cells in culture, and enhance the cytotoxicity of cytotoxic chemotherapeutic agents; SPM-924 (Schwarz Pharma), which is a tyrosine kinase inhibitor targeted for treatment of prostrate cancer; CP-546,989 (OSI Pharmaceuticals), which is reportedly an inhibitor of angiogenesis for treatment of solid tumors; ADL-681, which is a EGFR kinase inhibitor targeted for treatment of cancer; PD 158780, which is a pyridopyrimidine that is reported to inhibit the tumor growth rate of A4431 xenografts in mice; CP-358,774, which is a quinzoline that is reported to inhibit autophosphorylation in HN5 xenografts in mice; ZD1839, which is a quinoline that is reported to have antitumor activity in mouse xenograft models including vulvar, NSCLC, prostrate, ovarian, and colorectal cancers; CGP 59326A, which is a pyrrolopyrimidine that is reported to inhibit growth of EGFR-positive xenografts in mice; PD 165557 (Pfizer); CGP54211 and CGP53353 (Novartis), which are dianilnophthalimides. Naturally derived EGFR tyrosine kinase inhibitors include genistein, herbimycin A, quercetin, and erbstatin.

Further small molecules reported to inhibit EGFR are tricyclic compounds such as the compounds described in U.S. Pat. No. 5,679,683; quinazoline derivatives such as the derivatives described in U.S. Pat. No. 5,616,582; and indole compounds such as the compounds described in U.S. Pat. No. 5,196,446.

Further small molecules reported to inhibit EGFR are styryl substituted heteroaryl compounds such as the compounds described in U.S. Pat. No. 5,656,655. The heteroaryl group is a monocyclic ring with one or two heteroatoms, or a bicyclic ring with 1 to about 4 heteroatoms, the compound being optionally substituted or polysubstituted.

Further small molecules reported to inhibit EGFR are bis mono and/or bicyclic aryl heteroaryl, carbocyclic, and heterocarbocyclic compounds described in U.S. Pat. No. 5,646,153, the compound provided FIG. 1 of Fry et al., Science 265, 1093-1095 (1994) that inhibits EGFR, tyrphostins that inhibit EGFR/HER1 and HER 2, particularly those in Tables I, II, III, and IV described in Osherov et al., J. Biol. Chem., 25; 268(15):11134-42 (1993), the compound identified as PD166285 that inhibits the EGFR, PDGFR, and FGFR families of receptors, and PD166285, identified as 6-(2,6-dichlorophenyl)-2-(4-(2-diethylaminoethyoxy)phenylamino)-8-methyl-8H-pyrido(2,3-d)pyrimidin-7-one, having the structure shown in FIG. 1 on page 1436 of Panek et al., Journal of Pharmacology and Experimental Therapeutics 283, 1433-1444 (1997).

It should be appreciated that useful small molecule to be used in the invention are inhibitors of EGFR, but need not be completely specific for EGFR. As used herein "EGFR inhibitor" can refer to any agent capable of directly or indirectly inhibiting activation of EGFR. This can include compounds that directly inhibit the kinase activity of the EGFR or which inhibit the EGFR signal transduction pathway. In embodiments, an EGFR inhibitor can directly inhibit the kinase activity of the EGFR. In embodiments, the EGFR inhibitor is an antibody specific for EGFR, which can bind at any of the known domains of the receptor including the ligand binding domain or alternate binding sites within the known structure of the receptor. In other embodiments, the EGFR inhibitor is a small molecule, for example an EGFR-selective tyrosine kinase inhibitor. In embodiments an EGFR inhibitor can be Gefitinib (Iressa®) (Astrazeneca), Erlotinib (Tarceva®) (OSI), Cetuximab (Erbitux®) (Merck Serono), Panitumimab (Vectibix®)(Amgen) or other anti-EGFR inhibitors and mixtures thereof. In embodiments, EGFR inhibitors can include EGFR tyrosine kinase inhibitors as would be known in the art. In embodiments the EGRF inhibitor can be Cetuximab (Merck Serono) or Panitumimab (Amgen). In an embodiment the EGFR inhibitor can be Cetuximab (Merck Serono). Cetuximab (IMC-C225) is a chimeric (human/mouse) IgG monoclonal antibody, also known under the tradename ERBITUX. In addition, the agent may target other members of the EGFR receptor family, including the use of Herceptin to target ErbB2 in breast cancer.

"Chemotherapy" as used herein can include DNA-alkylating agents, antimetabolites, microtubule distrupters, DNA intercalators and hormone therapy. In embodiments, chemotherapy can include but not limited to cisplatin, oxaliplatin, carboplatin, irinotecan, or taxane-therapy, depending on tumour-type that the subject is afflicted with.

"Antibody" as used herein includes intact immunoglobulin molecules, as well as fragments thereof, such as Fab, F(ab')2 and Fv, which are capable of binding to an epitope of CXCR1.

"Tumour", as used herein, refers to any neoplastic cell growth and proliferation, whether malignant or benign, and all pre-cancerous and cancerous cells and tissues.

"Cancer" as used herein is a generic name for a wide range of cellular malignancies characterized by unregulated growth, lack of differentiation, and the ability to invade local tissues and metastasize. These neoplastic malignancies can affect various tissues and organs of the body, for example, colorectal cancer, breast cancer, ovarian cancer, lung cancer, prostate cancer, hepatocellular cancer, gastric cancer, pancreatic cancer, cervical cancer, liver cancer, bladder cancer, cancer of the urinary tract, thyroid cancer, renal cancer, carcinoma, melanoma, brain cancer, non-small cell lung cancer, squamous cell cancer of the head and neck, endometrial cancer, multiple myeloma, rectal cancer, and esophageal cancer. In a particular embodiment, the cancer is colorectal cancer.

The terms "subject" and "patient" are used interchangeably herein to refer to a mammal being assessed for treatment and being treated. In an embodiment, the mammal is a human.

The terms "treatment", treating" and the like refer to the administration of an agent for the purpose of obtaining an effect. The effect may be prophylactic and/or may be therapeutic. By "therapeutic" as used herein is meant the abrogation or alleviation of a cancer. This means the survival or life expectancy of the cancer patient will be increased or that one or more symptoms of the cancer are reduced. For example, this can encompass a reduction in the cancer growth rate or tumour volume. Assessment of tumour volume can be by imaging a cancer patient as would be known in the art.

Each document, reference, patent application or patent cited in this text is expressly incorporated herein in their entirety by reference, which means it should be read and considered by the reader as part of this text. That the document, reference, patent application or patent cited in the text is not repeated in this text is merely for reasons of conciseness.

Reference to cited material or information contained in the text should not be understood as a concession that the material or information was part of the common general knowledge or was known in any country.

Throughout the specification, unless the context demands otherwise, the terms 'comprise' or 'include', or variations such as 'comprises' or 'comprising', 'includes' or 'including' will be understood to imply the includes of a stated integer or group of integers, but not the exclusion of any other integer or group of integers.

An embodiment of the present invention will now be described by way of example only, with reference to the accompanying figures.

Figure 8:
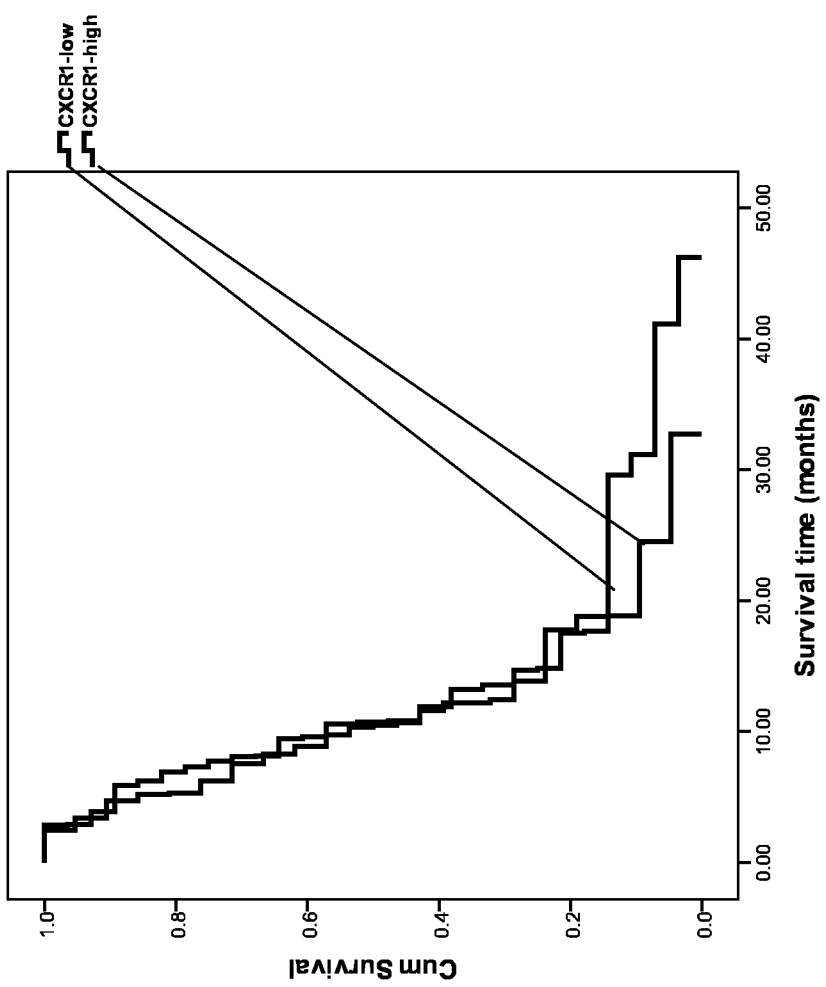
Figure 10:
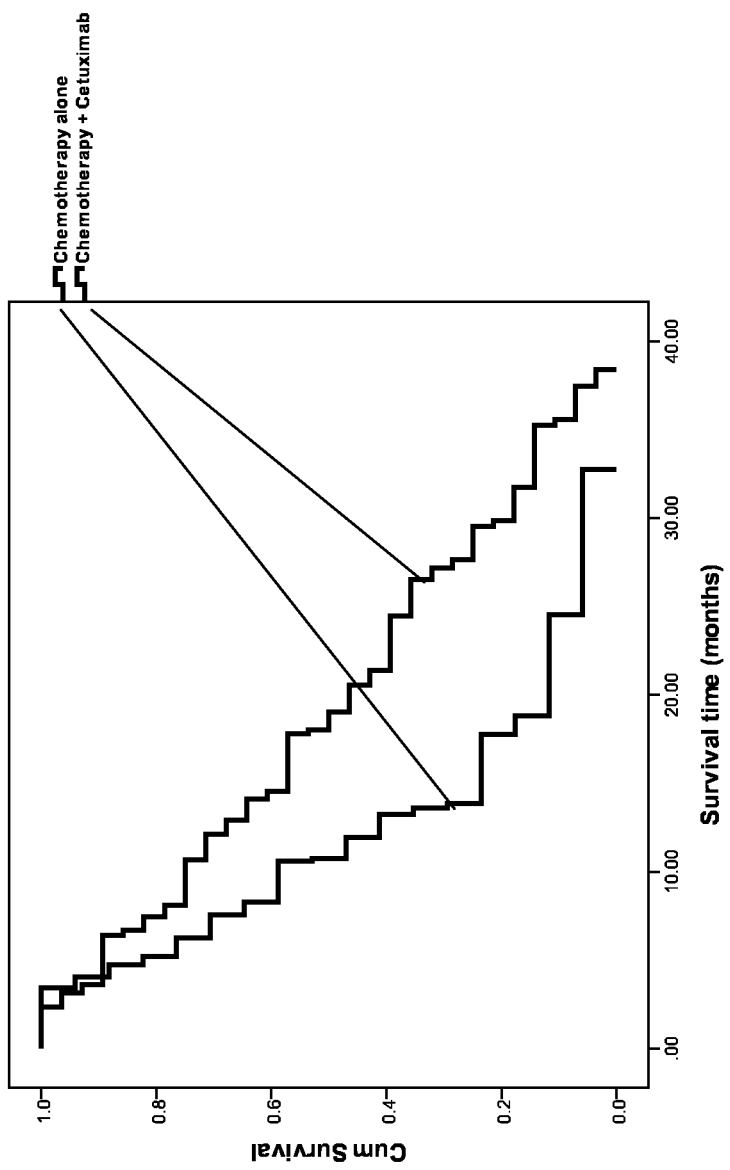
Figure 12:
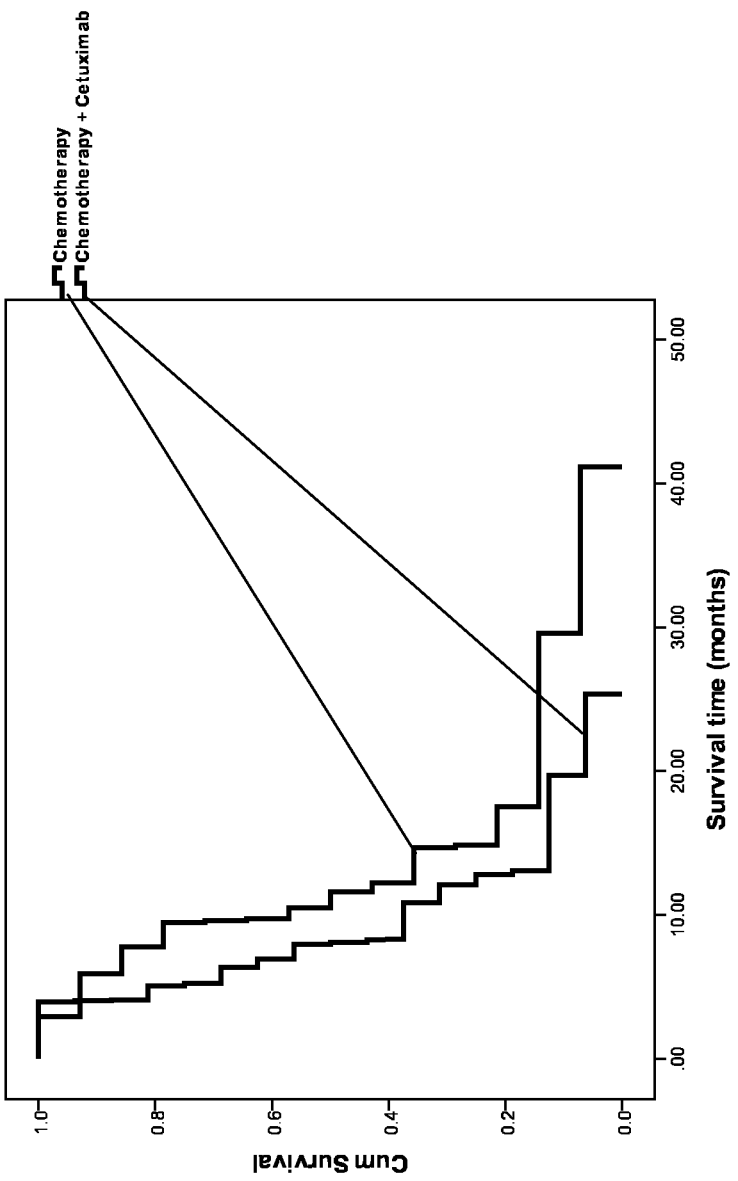

FIG. 1 illustrates Table 1 the characterization of the patient cohort,

FIG. 2 illustrates Table 2. Multivariate logistic regression for response at 12 weeks, FIG. 3 illustrates Table 3. Multivariate logistic regression for response at any time, FIG. 4 illustrates Table 4. Univariate survival analysis, FIG. 5 illustrates Table 5. Multivariate survival analysis, FIG. 6 illustrates survival analysis of patients treated with Cetuximab, randomized for CXCR1 expression levels (18 CXCR1-low, 29 CXCR1-high), FIG. 7 illustrates Table 6. Prognostic impact of CXCR1 in Cetuximab-treated patients, FIG. 8 illustrates survival analysis of patients who did not receive Cetuximab, randomized for CXCR1 expression levels (35 CXCR1-low, 27 CXCR1-high), FIG. 9 illustrates Table 7. Prognostic impact in non-Cetuximab treated patients, FIG. 10 illustrates high CXCR1 expression predicts for clinical benefit of adding Cetuximab to oxaliplatin/5-FU chemotherapy (n=55 patients with high CXCR1 expression:), FIG. 11 illustrates Table 8. Role of high CXCR1 expression as predictive marker of response to Cetuximab treatment, FIG. 12 illustrates Low CXCR1 expression fails to predict the clinical benefit of adding Cetuximab to oxaliplatin/5-FU chemotherapy (38 patients had low CXCR1 expression), and FIG. 13 illustrates Table 9. Patient response data to treatment in patients with low CXCR1 expression.

DETAILED DESCRIPTION OF THE INVENTION

Based on a national phase III trial which investigated the response of >2500 patients with metastatic colorectal cancer who were randomized to
 chemotherapy alone,
 the provision of intermittent chemotherapy, or
 chemotherapy in combination with Cetuximab, a monoclonal antibody targeting the EGFR receptor
the relationship of CXC-chemokine and CXC-chemokine receptor expression in relation to the clinical response of colorectal cancer to EGFR therapeutics was considered.

The tissues analysed were obtained from the COIN trial, which was based on provision of chemotherapy (oxaliplatin/5-FU based) and the EGFR-targeted antibody Cetuximab (Merck Serono).

Example 1

Relationship Between CXCR1 and K-Ras Mutational Status

In total, 116 tissue samples were obtained from the Central Processing Resource of the COIN phase III clinical trial under ethical consent. Data regarding patient age, gender, K-Ras status, response and patient status was obtained at the time of analysis. Consistent with independent reports regarding the incidence of K-Ras mutations in colorectal cancer, 38% of the tumours in which the status of this protein had been evaluated were found to have a mutation in the protein. Only 10 cases did not have an accompanying characterization of KRas protein. The patient data is presented in Table 1.

Logistic regression analysis determined that the expression of CXCR1 was independent of K-Ras mutational status in colorectal cancer tissue (P=0.215).

Example 2

Relationship Between CXCR1 Expression and Tumour Response

The next analysis was to determine the relationship of clinical parameters in relation to the observation of a Multivariate analysis of data of tumour response in patients, assessed 12 weeks after the onset of treatment, determined that higher CXCR1 expression in the tumour epithelium correlated with an increased tumour response at 12 weeks (p=0.005). In addition, patients treated with Cetuximab had an improved response at 12 weeks if they had high levels of CXCR1 expression (p=0.019). Interestingly, the correlation of response in Cetuximab-treated patients to CXCR1 was more significant than the correlation to KRas-status in this cohort of patients (p=0.053) (Table 2).

Subsequent multivariate analysis was conducted to analyse parameters against the observation of a clinical response of the patient to treatment at any time. Higher tumour epithelial CXCR1 expression again correlated with the observation of a favourable clinical response (p=0.027) and an increased response in patients treated with Cetuximab (p=0.05). As observed in the analysis of response after 12 weeks, KRas-status was not predictive of response to Cetuximab in this cohort of patients (p=0.099) (Table 3).

Example 3

Assessment of Clinical Parameters Against the Survival of Patients

Survival was independent of the Treatment Arm within the trial, while patient age borders on significance. Tumour epithelial CXCR1 expression or the level of CXCL8 expression within the inflammatory infiltrate did not correlate with improved patient survival across the cohort, in univariate analysis. However, high CXCR1 expression did correlate with an improved survival in those patients treated with Cetuximab (p=0.007). In contrast, K-Ras status was not associated with overall survival (p=0.305) or indeed response to Cetuximab (p=0.746) (Table 4). Conduct of a multivariate analysis confirmed that high CXCR1 expression correlated with an improved overall survival in patients treated with Cetuximab (p=0.019) (Table 5).

Example 4

Prognostic Impact of CXCR1 Expression in Patients Treated with Cetuximab

Patients were stratified to two cohorts on the basis of high or low CXCR1 expression, which was assessed using the median expression level as the discriminating threshold. Following this stratification, 18 patients who had received Cetuximab were considered to have low CXCR1 expression while 29 patients had high CXCR1 expression. Patients with low CXCR1 expression had a median overall survival of 7.97 months, while patients with high CXCR1 expression had a median overall survival of 19.033 months (p=0.001) (FIG. 6; Table 6). In a parallel assessment conducted in patients who did not receive Cetuximab, there was no difference in the median overall survival of patients with low CXCR1 expression (10.33 months) or high CXCR1 expression (10.73 months) (FIG. 8; Table 7). Together these analyses show the specificity of CXCR1 expression in relation to patient survival in Cetuximab-treated patients.

Example 5

Capacity of CXCR1 Expression to Predict the Clinical Outcome of Patients to Cetuximab Therapy Analysis of patients that had received either chemotherapy alone or chemotherapy in combination with Cetuximab determined low CXCR1 expression in 38 patients, of which 18 patients received Cetuximab in addition to chemotherapy. In patients with low CXCR1 expression, the addition of Cetuximab actually had an adverse effect on the overall survival of these patients, reducing median overall survival from 10.5 months to 7.97 months (FIG. 12; Table 9).

Analysis of patients with high tumour CXCR1 expression levels had a very different profile. In the 55 patients with high CXCR1 expression, 33 patients received Cetuximab in combination with chemotherapy. In these patients, the addition of Cetuximab improved overall survival from 10.73 months to 18.03 months (p=0.013) (FIG. 10; Table 8). Therefore, this data clearly reveals that high tumour CXCR1 expression predicts for those patients that will derive a clinical benefit from the provision of Cetuximab to an oxaliplatin/5-fluorouracil-based chemotherapy regimen.

In summary, that analysis indicated the CXCR1 chemokine receptor is a strong prognostic factor and a predictive marker of patient response to Cetuximab in colorectal cancer.

In the above examples expression of CXCR1 was determined using an optimized immunohistochemistry protocol, exploiting a commercially-available CXCR1 monoclonal antibody).

Although the invention has been particularly shown and described with reference to particular examples, it will be understood by those skilled in the art that various changes in the form and details may be made therein without departing from the scope of the present invention.

Sequence Listing

The nucleic acid and amino acid sequences of the CXCR1 gene and protein described herein are provided below. Further refinements and/or characterization of additional transcripts that are given the assignment of these gene names are considered to be included under the scope of the claims, and in addition, existing or defined polymorphisms and/or mutations of these genes are included in the definitions of these genes and to be under the scope of the claims filed under this patent application.

Molecular Definition of CXCR1

The nucleotide sequence of CXCR1 is accessible in public databases by the accession number NM_000634 and is provided herein as SEQ ID NO: 1. In embodiments the term CXCR1 includes active forms of CXCR1 and active fragement thereof.

SEQ ID NO: 1

```
tattcatcaa gtgccctcta gctgttaagt cactctgatc tctgactgca gctcctactg ttggacacac ctggccggtg cttcagttag atcaaaccat tgctgaaact gaagaggaca tgtcaaatat tacagatcca cagatgtggg attttgatga tctaaatttc actggcatgc cacctgcaga tgaagattac agcccctgta tgctagaaac tgagacactc aacaagtatg ttgtgatcat cgcctatgcc ctagtgttcc tgctgagcct gctgggaaac tccctggtga tgctggtcat cttatacagc agggtcggcc gctccgtcac tgatgtctac ctgctgaacc tggccttggc cgacctactc tttgccctga ccttgccat ctgggccgcc tccaaggtga atggctggat ttttggcaca ttcctgtgca aggtggtctc actcctgaag gaagtcaact tctacagtgg catcctgctg ttggcctgca tcagtgtgga ccgttacctg gccattgtcc atgccacacg cacactgacc cagaagcgtc acttggtcaa gtttgtttgt cttggctgct ggggactgtc tatgaatctg tccctgccct tcttcctttt ccgccaggct taccatccaa acaattccag tccagtttgc tatgaggtcc tgggaaatga cacagcaaaa tggcggatgg tgttgcggat cctgcctcac acctttggct tcatcgtgcc gctgtttgtc atgctgttct gctatggatt caccctgcgt acactgttta aggcccacat ggggcagaag caccgagcca tgagggtcat ctttgctgtc gtcctcatct tcctgctttg ctggctgccc tacaacctgg
```

```
tcctgctggc agacaccctc atgaggaccc aggtgatcca ggagagctgt gagcgccgca acaacatcgg ccgggccctg gatgccactg agattctggg atttctccat agctgcctca accccatcat ctacgccttc atcggccaaa attttcgcca tggattcctc aagatcctgg ctatgcatgg cctggtcagc aaggagttct tggcacgtca tcgtgttacc tcctacactt cttcgtctgt caatgtctct tccaacctct gaaaaccatc gatgaaggaa tatctcttct cagaaggaaa gaataaccaa caccctgagg ttgtgtgtgg aaggtgatct ggctctggac aggcactatc tgggttttgg ggggacgcta taggatgtgg ggaagttagg aactggtgtc ttcaggggcc acaccaacct tctgaggagc tgttgaggta cctccaagga ccggcctttg cacctccatg gaaacgaagc accatcattc ccgttgaacg tcacatcttt aacccactaa ctggctaatt agcatggcca catctgagcc ccgaatctga cattagatga gagaacaggg ctgaagctgt gtcctcatga gggctggatg ctctcgttga ccctcacagg agcatctcct caactctgag tgttaagcgt tgagccacca agctggtggc tctgtgtgct ctgatccgag ctcagggggg tggttttccc atctcaggtg tgttgcagtg tctgctggag acattgaggc aggcactgcc aaaacatcaa cctgccagct ggccttgtga ggagctggaa acacatgttc cccttggggg tggtggatga acaaagagaa agagggtttg gaagccagat ctatgccaca agaaccccct ttaccccccat gaccaacatc gcagacacat gtgctggcca cctgctgagc cccaagtgga acgagacaag cagcccttag cccttcccct ctgcagcttc caggctggcg tgcagcatca gcatccctag aaagccatgt gcagccacca gtccattggg caggcagatg ttcctaataa agcttctgtt ccgtgcttgt ccctgtggaa gtatcttggt tgtgacagag tcaagggtgt gtgcagcatt gttggctgtt cctgcagtag aatgggggca gcacctccta agaaggcacc tctctgggtt gaagggcagt gttccctggg gctttaactc ctgctagaac agtctcttga ggcacagaaa ctcctgttca tgcccatacc cctggccaag gaagatccct ttgtccacaa gtaaaaggaa atgctcctcc agggagtctc agcttcaccc tgaggtgagc atcatcttct gggttaggcc ttgcctaggc atagccctgc ctcaagctat gtgagctcac cagtccctcc ccaaatgctt tccatgagtt gcagtttttt cctagtctgt tttccctcct tggagacagg gccctgtcgg tttattcact gtatgtcctt ggtgcctgga gcctactaaa tgctcaataa ataatgatca caggaaaaaa aaaaaaaaa aa
```

The amino acid sequence of CXCR1 is provided herein as SEQ ID NO: 2.

MSNITDPQMWDFDDLNFTGMPPADEDYSPCMLETETLNKYVVIIAYALVFLLSLLGNSLV

MLVILYSRVGRSVTDVYLLNLALADLLFALTLPIWAASKVNGWIFGTFLCKVVSLLKEVNF

YSGILLLACISVDRYLAIVHATRTLTQKRHLVKFVCLGCWGLSMNLSLPFFLFRQAYHPNN

SSPVCYEVLGNDTAKWRMVLRILPHTFGFIVPLFVMLFCYGFTLRTLFKAHMGQKHRAM

RVIFAVVLIFLLCWLPYNLVLLADTLMRTQVIQESCERRNNIGRALDATEILGFLHSCLNPII

YAFIGQNFRHGFLKILAMHGLVSKEFLARHRVTSYTSSSVNVSSNL

---

The invention claimed is:

1. A method of predicting response in a cancer subject to treatment with an Epidermal Growth Factor Receptor (EGFR) targeted therapeutic, wherein the EGFR targeted therapeutic is an EGFR targeted antibody or small molecule EGFR inhibitor, the method comprising using CXCR1 as a biomarker, comprising the steps of
   determining in a tumour sample from the cancer subject an expression level of CXCR1;
   comparing the determined expression level of CXCR1 in the tumour sample from the cancer subject with an expression level of CXCR1 in a Control, wherein when the expression level of CXCR1 determined in the tumour sample from the cancer subject is increased from that of the expression level of CXCR1 in the Control the expression level of CXCR1 is indicative the cancer subject would benefit from treatment with an Epidermal Growth Factor Receptor targeted therapeutic; and
   administering a therapeutically effective amount of an EGFR targeted therapeutic to the subject if the subject has an expression level of CXCR1 increased from that of an expression level of a Control.

2. The method as claimed in claim 1 wherein the Control is a control population of cancer subjects and the expression level of CXCR1 in the Control is the median expression level of CXCR1 in the control population.

3. The method as claimed in claim 1, wherein the tumour is selected from the group consisting of a colorectal tumour, a NSCLC tumour, a head and neck tumour, and an ovarian tumour.

4. The method as claimed in claim 1, wherein the Epidermal Growth Factor Receptor targeted therapeutic is selected from at least one of Cetuximab, Panitumumab, Gefitinib, and Tarceva.

5. The method as claimed in claim 1 wherein the Epidermal Growth Factor Receptor targeted therapeutic is at least one of Cetuximab or Panitumumab.

6. The method as claimed in claim 5 wherein the Epidermal Growth Factor Receptor targeted therapeutic is Cetuximab.

7. The method as claimed in claim 5 wherein the Epidermal Growth Factor Receptor targeted therapeutic is at least one of Cetuximab or Panitumumab and is provided as a monotherapy.

8. The method as claimed in claim 5, wherein the subject is treated with at least one of Cetuximab or Panitumumab in combination with a clinically-approved conventional cytotoxic chemotherapy agent.

9. The method as claimed in claim 1, wherein the step of determining the expression level comprises as least one of:
   determining a protein expression level of CXCR1;
   determining a level of mRNA encoding CXCR1;
   determining a copy number of CXCR1; and
   determining an expression level of any non-coding or coding polymorphism within a nucleotide sequence CXCR1.

10. The method as claimed in claim 1, wherein the tumor sample is a tumor tissue sample.

11. The method of claim 1 further comprising the step of determining that the subject is responsive to the EGFR targeted therapeutic by measuring the level of CXCR1 in a tumor sample in the subject after administration of the EGFR targeted therapeutic.

* * * * *